(12) United States Patent
Bader (10) Patent No.: US 9,101,586 B2
(45) Date of Patent: Aug. 11, 2015

(54) TOPICAL APPLICATION AND FORMULATION OF ERYTHROPOIETIN FOR SKIN WOUND HEALING

(75) Inventor: Augustinus Bader, Parthenstein OT Klinga (DE)

(73) Assignee: Augustine Bader (DE)

( * ) Notice: Subject to any disclaimer, the term of this patent is extended or adjusted under 35 U.S.C. 154(b) by 506 days.

(21) Appl. No.: 12/810,711

(22) PCT Filed: Dec. 20, 2008

(86) PCT No.: PCT/EP2008/010978
§ 371 (c)(1),
(2), (4) Date: Jun. 25, 2010

(87) PCT Pub. No.: WO2009/083203
PCT Pub. Date: Jul. 9, 2009

(65) Prior Publication Data
US 2010/0278916 A1    Nov. 4, 2010

(30) Foreign Application Priority Data

Dec. 28, 2007  (EP) .................................. 07025167

(51) Int. Cl.
| | | |
|---|---|---|
| A61K 38/18 | (2006.01) | |
| A61K 31/717 | (2006.01) | |
| A61P 17/02 | (2006.01) | |
| C07K 14/505 | (2006.01) | |
| A61K 9/00 | (2006.01) | |
| A61K 9/06 | (2006.01) | |
| A61K 47/10 | (2006.01) | |
| A61K 47/32 | (2006.01) | |
| A61K 47/38 | (2006.01) | |
| A61L 15/44 | (2006.01) | |
| A61L 26/00 | (2006.01) | |

(52) U.S. Cl.
CPC ........... *A61K 38/1816* (2013.01); *A61K 9/0014* (2013.01); *A61K 9/06* (2013.01); *A61K 47/10* (2013.01); *A61K 47/32* (2013.01); *A61K 47/38* (2013.01); *A61L 15/44* (2013.01); *A61L 26/0066* (2013.01); *A61L 2300/252* (2013.01); *A61L 2300/404* (2013.01); *A61L 2300/41* (2013.01); *A61L 2300/412* (2013.01); *A61L 2300/434* (2013.01)

(58) Field of Classification Search
USPC .......... 424/455, 488, 78.06; 536/56; 514/781, 514/649
See application file for complete search history.

(56) References Cited

U.S. PATENT DOCUMENTS

| | | | |
|---|---|---|---|
| 2005/0187158 A1* | 8/2005 | Ranby | 514/12 |
| 2005/0281881 A1* | 12/2005 | Woeller et al. | 424/487 |
| 2006/0045912 A1* | 3/2006 | Truog | 424/468 |
| 2007/0275882 A1* | 11/2007 | Meijer et al. | 514/8 |
| 2008/0247987 A1* | 10/2008 | Liggins et al. | 424/78.17 |

FOREIGN PATENT DOCUMENTS

| | | |
|---|---|---|
| WO | WO 93/25221 A1 | 12/1993 |
| WO | WO 97/07788 A2 | 3/1997 |
| WO | WO 03/053471 A1 | 7/2003 |
| WO | WO 2004/001023 A2 | 12/2003 |
| WO | WO 2005/063965 A1 | 7/2005 |
| WO | WO 2005/070451 A1 | 8/2005 |
| WO | WO 2006/089056 A2 | 8/2006 |

\* cited by examiner

*Primary Examiner* — Joanne Hama
*Assistant Examiner* — Regina M Deberry
(74) *Attorney, Agent, or Firm* — Ronald J. Kamis; The Law Office of Ronald J. Kamis

(57) ABSTRACT

The invention relates to the use of erythropoietin (EPO), in particular EPO in a polymer-based pharmaceutical preparation which stabilizes the active compound, for the treatment of traumatized skin, in particular for wound healing in the case of mechanical or pathological injuries or in the case of burns.

In particular, the invention also relates to specific viscous or gelatinous formulations, in particular based on polysaccharides, preferably cellulose derivatives, which comprise EPO and are capable of stabilizing the latter and releasing it slowly and uniformly to the wound.

12 Claims, 6 Drawing Sheets

TOPICAL APPLICATION AND FORMULATION OF ERYTHROPOIETIN FOR SKIN WOUND HEALING

CROSS-REFERENCE TO RELATED APPLICATION

This application is a 371 National Stage entry of International Application No. PCT/EP2008/010978, filed Dec. 20, 2008, published as WO 2009/083203 with an International Publication Date of Jul. 9, 2009, which claims priority to European Patent Application No. 07025167.3 filed Dec. 28, 2007. These prior applications are hereby incorporated by reference herein in their entirety.

TECHNICAL AREA OF THE INVENTION

The invention relates to the use of erythropoietin (EPO), in particular EPO in a pharmaceutical preparation which stabilises the active compound, for the topical treatment of traumatised skin, in particular for wound healing in the case of mechanical or pathological injuries or in the case of burns. In particular, the invention is directed to the use of EPO in a stabilised form according to the invention based on hydrophilic polymers for stimulation of differentiation and growth of certain cell types, for example tissue-specific precursor cells which are not vascular precursor cells, or of adult tissue-specific cells which are not endothelial cells, which are in each case encountered in the immediate wound region in the case of skin injuries of this type.

In particular, the invention also relates to specific viscous or gelatinous formulations based on polysaccharides, in particular cellulose derivatives, which comprise EPO and are capable of stabilising the latter and releasing it slowly and uniformly to the wound.

TECHNICAL BACKGROUND OF THE INVENTION

Erythropoietin (EPO) is a glycoprotein hormone which controls the formation of erythrocytes from precursor cells in the bone marrow (erythropoiesis). EPO binds here to its receptor (EPO-R), which is expressed in all haemopoietic cells.

In adults, erythropoietin is formed principally in the kidney, more precisely in the endothelial cells of the peritubular capillaries. Relatively small amounts are also synthesised in the liver cells (hepatocytes).

The principal action of EPO thus consists in increasing the number of red blood corpuscles in the blood, which results in increased oxygen uptake.

In recent years, diverse authors have reported that EPO also exerts a non-haemopoietic action and EPO-R is correspondingly also expressed by certain non-haemopoietic cells. Thus, stimulation by EPO of nerve cells, neuronal cells of the brain and endothelial cells is reported, in some cases together with direct expression of the haemopoietic EPO receptor. In other cases, the presence of a further, non-haemopoietic receptor is prognosticated, but this has not yet been proven.

Increasing importance is being accorded, in particular, to the non-haemopoietic action, which has not been known for very long, of erythropoietin (EPO) in connection, for example, with the stimulated formation and regeneration of endothelial and tissue cells, such as connective tissue, muscle tissue, epithelial tissue and nerve tissue.

Thus, WO 2004/001023 describes, inter alia, the use of EPO and TPO for stimulating neovascularisation and tissue regeneration and improving wound healing, for example after operations or injuries.

WO 2005/063965 teaches the use of EPO for the targeted, structurally controlled regeneration of traumatised tissue, in which not only is endothelial cell growth stimulated, but parenchymal regeneration and the formation of wall structures are also promoted, meaning that coordinated three-dimensional growth occurs for the construction of a functioning tissue, organ or parts thereof.

Haroon et al. (American J. Pathol. 2003, 163, 993) discuss the new role of EPO in the context of wound healing processes induced by fibrin.

In a review article, Brines and Cerami (Kidney International, 2006) discuss the role of EPO in the protection of tissue.

Erythropoietin, and EPO derivatives or also EPO mimetics, thus appear to be highly suitable on systemic use for specifically initiating and controlling neoformation and regeneration of the affected tissue in the case of injuries to the skin, the mucous membrane, in the case of open skin and flesh wounds or also in the case of skin irritation caused by burns or scalds, and is ultimately able to promote and accelerate healing.

WO 2005/070450 and further papers by the inventors in question describe the use of EPO in the regeneration of vessels and tissue with a weekly dose of less than 90 IU/kg of body weight (=BW), including for the area of wound care. Although possible topical application is theoretically mentioned here, it has nevertheless been found that systemic application is preferred.

It is therefore postulated to administer EPO in the case of systemic application in a sub-polycythemic weekly dose of less than 90 IU (international units)/kg of body weight (BW) instead of 150-300 IU/kg of BW, as was hitherto usual for the known EPO applications. The aim is thus to achieve less stimulation of blood formation in the bone marrow region, but, according to more recent teaching, as outlined, to enable activation of endothelial cell progenitors in the blood region. Activation of the endothelial cell precursor cells in the blood, but also in the tissue, and the development of endothelial cells, which form the innermost cell layer of the blood vessels, have been connected with an improvement in vascularisation, and it is assumed that tissue regeneration is also facilitated thereby. In the meantime, this has been confirmed in clinical trials in the case of burn wounds.

Although some of the said papers mention topical application of EPO for the regeneration of tissue, systemic application of the active compound is, however, placed clearly in the foreground since, on the basis of the results, the non-haemopoietic EPO effect found can be attributed, in the opinion of more recent papers, primarily to the newly discovered stimulation of corresponding endothelial, vascular or CD31-positive precursor cells, which circulate principally with the blood stream, and only secondarily to the growth of parenchymal tissue structures stimulated thereby.

However, the use of EPO in a systemic application for tissue protection or tissue regeneration is associated with significant risks owing to the side-effect potential in relation to the haemopoietic effects.

On topical application of EPO, according to teaching opinion to date, merely the inadequate distribution and reachability of the said systemically occurring cells or precursor cells by EPO means that only an unsatisfactory effect, or none at all, on tissue regeneration would be observed.

In the case of regeneration of tissues after, for example, burn trauma or scalding or also in the case of ischaemic wounds, it is necessary to achieve rapid defect closure. This can only occur if the formation of the parenchymal components of the skin is also stimulated as quickly as possible. The time-shifted stimulation of one component (CD31), in order then to facilitate the formation of another component (parenchyma), corresponds to the teaching of the authors of WO 2005/070450 and further publications.

Although the formation of a vascular network can have an indirect supporting action, it does not as such represent an end result, since the parenchyma is missing and under certain circumstances can only be formed secondarily and thus with a time delay.

The formation of vascular cells must thus be coordinated simultaneously with localised tissue formation. In this case, in accordance with conventional teaching, a dilemma occurs, since doses administered subcutaneously or intravenously target endothelial cell progenitors owing to a systemic distribution principle, and sub-polycythemic doses must additionally be administered in order to limit side effects. In this case, the administration of EPO can thus only be combined with difficulty with localised pharmacokinetics limited locally to the trauma region of the skin.

In accordance with conventional teaching, conceptional stimulation pathways must therefore be selected, where either sub-polycythemic doses must be administered or repeated injections or also changes in the half-value period of the parent substance are necessary.

In each case, however, EPO will arrive at the actual site of need via the bloodstream systemically distributed in the body and even further diluted.

Furthermore, processes occur in the case of wounds which make topical application of EPO more difficult: wound healing of, for example, injured skin or mucous membrane usually proceeds in three phases: the inflammation phase, the proliferation phase and the restoration/remodelling phase. In the case of a fresh wound or skin injury to be cared for, inflammatory processes occur within the first 24 hours, which include, in particular, the immigration of diverse inflammation factors (such as, for example, fibronectin) and cells of various types, such as, for example, monocytes, phagocytes, polymorphic cells and macrophages, and ultimately result in the formation of a fibrin matrix and vascular endothelial cells. The wound secretion formed in the process comprises, inter alia, a series of proteolytic enzymes as well as bacteria which have entered the wound and comprise substances which act in this respect.

The proteolytic enzymes, some of which are highly active, are the reason why protein- or peptide-containing medicaments, such as EPO, which have been applied to the wound and promote wound healing are often of little or no efficacy, since the protein or polypeptide in question is, owing to its chemical and biological nature, deactivated, cleaved and degraded by said enzymes before it is able to develop adequate pharmacological efficacy. The problem is additionally exacerbated by infection of the wound with bacteria or the ingress of cell debris.

Not least for this reason, pharmaceutical proteins are generally applied systemically, which enables their half-value period to be significantly extended and also enables them to be transported more quickly to the sites in the body at which they are to develop their therapeutic efficacy. However, the doses of the protein-containing active compound must be sufficiently high in this application method in order to achieve the desired therapeutic effect, which often inevitably results in undesired side reactions.

In the case of the therapeutic treatment of skin injuries, systemic application of an active compound moreover in principle appears less appropriate, since the healing action of the medicament is actually only necessary locally. There is thus a general problem if protein-containing active compounds are to be employed for the treatment of skin injuries and open flesh and skin wounds.

The use of proteins or polypeptides in topical form, such as, for example, EPO, which, even in plasma, has a half-value period of only 48 hours, for the treatment of skin injuries of this type, as may occur in the case of violent mechanical trauma and irritation and in the case of burns and scalds, would, however, be very desirable in spite of the known difficulties.

The object is thus to provide EPO or its bioequivalent derivatives, fragments, mimetics and the like for skin wound healing in the form of a topical application, without on the one hand, as just described, dramatic losses of action occurring due to proteolysis of EPO due to enzymatic or other processes in the wound, but on the other hand, as likewise explained in detail above, possibly facilitating stimulation of cells or precursor cells which are capable of wound healing in the immediate wound region and if possible also in deeper tissue layers in the vicinity of the wound by topically applied EPO, which ultimately should result in faster wound closure and makes topical application of EPO appear sensible for the first time and provides it with a significant advantage over systemic administration.

A further aim of the invention is to create a form of administration which does not have to take into account the risks and restrictions of a systemic, in particular sub-polycythemic dosage of EPO, and at the same time can act specifically on the actual tissue-relevant cells without at the same time excluding the localised adult endothelial cells.

SUMMARY OF THE INVENTION

Surprisingly, it has now been found that, on topical application, preferably in a suitable formulation which stabilises the active compound and releases it uniformly, EPO is effective in the case of injuries or pathologically induced damage to the skin, where this efficacy, as also shown, in particular, by histological studies, is not or virtually not attributable to the known prognosticated activation of endothelial and other precursor cells which circulate in the blood and may be transported to the wound—this would not be sufficient for the target effect—but instead is apparently based on EPO-induced stimulation of cells which have accumulated locally, i.e. in the immediate wound region or in the extended vicinity of the wound, where, surprisingly, the cells in the skin tissue which contribute functionally to wound healing are predominantly those which are parenchymal, i.e. are not vascular cells or precursor cells thereof and also are predominantly not endothelial cells or precursor cells thereof which are located in the wound tissue.

In general, it has been found that, in particular, the cells in the wound region which do not carry or express the endothelial cell surface marker CD31, or only do so to a slight extent, are stimulated to differentiation and growth directly and locally by topically applied EPO.

CD31 is usually found on endothelial cells or vascular cells, platelets, macrophages, granulocytes, T-cells, NK-cells, lymphocytes and fibroblasts. CD31-expressing cells are regarded as neoangiogenesis factors. In tissues, the vessels are structures which run through the tissue like rivers, but in no way represent the tissue itself. These vascular cells and precursor cells thereof have surface markers, such as CD31, enabling these to be precisely differentiated and delimited from other types of cell. Parenchymal components of the skin are CD31-negative cell types, such as keratinocytes, hair root cells and dermal cells, such as connective-tissue cells. CD31-negative cells, in particular keratinocytes, hair root cells and connective-tissue cells, or cells which only express CD31 to a slight extent are preferably thus stimulated directly and locally by locally applied EPO. This further action effect is novel and differs both from the known haemopoietic EPO effect and also from the non-haemopoietic mechanism, which was recently discovered and demonstrated systemically (see above).

It should be emphasized in this connection that, in particular, the systemic application of erythropoietin and derivatives and analogues thereof in the case of subcutaneous or intravenous administration only causes an inadequate or excessively short effect at the site of the injury to the skin, especially as this systemic concept neglects the importance of the tissue-specific stem cells, which are completely independent of vascular cells.

In accordance with the invention, the localised precursor cells in skin appendages and the stem-cell crypts of the skin can thus be stimulated directly by topical administration of EPO for the first time. It has furthermore been found that CD90-positive cells and nestin-positive cells in the wound region of the skin are also stimulated via the EPO-induced stimulation of the said substantially CD31-negative cells. CD90 is a marker protein for stem cells and neuronal precursor cells, while nestin is a marker for nerve cells. CD73-positive cells in the wound region are also co-stimulated directly by EPO. Topically applied EPO is thus capable of stimulating virtually all important cells in the immediate wound region which are essential for skin wound healing to growth.

In accordance with the invention, totally irrespective of the specifications and restrictions of sub-polycythemic dosage requirements of the prior art, direct stimulation of essential cells and precursor cells which are specific to wound healing in the skin is effected on use of topically applied EPO, preferably in a suitable formulation based on polymers, in particular hydrophilic polymers, and derivatives and analogues thereof having the same action or a similar action. This occurs irrespective of an action on endothelial cell progenitors throughout the organism which unavoidably takes place in the case of a conventional systemic application form. A systemic action of this type is generally undesired owing to the haemopoietic effects which occur (increase in the number of red blood cells, increased blood formation in the bone marrow, increased risk of thrombosis, etc.).

Topically and locally applied EPO in accordance with the invention furthermore causes no or substantially no stimulation of vascular or endothelial precursor cells circulating systemically in the bloodstream. Direct stimulation of the cells close to the wound has the advantage that the regional skin and wound environment on the one hand restricts systemic resorption by, for example, proteases, which reduces the degradation of EPO before entry into the systemic circulation area and nevertheless facilitates a locally high active-compound concentration. EPO amounts which would mean a concentration of 250 IU of EPO/BW or more in the case of a conventional systemic application form can readily be administered without the corresponding undesired EPO effects mentioned occurring. This considerably broadens the therapeutic window for the area of tissue regeneration. In addition, co-stimulatory effects may be initiated by the trauma cytokines, which are only present locally in high concentrations, due to the topical administration of EPO.

The invention thus relates to:

the use of erythropoietin or one of its derivatives or analogues having the same biological action (EPO), preferably in the form of a pharmaceutical formulation which stabilises the active compound and liberates it uniformly and is preferably based on polymers having at least partially hydrophilic properties, for the preparation of a medicament to be applied topically and locally for defect closure and/or for re-epithelialisation of traumatised skin by targeted stimulation of tissue-specific precursor cells which are not vascular precursor cells and of adult tissue-specific cells which are not endothelial cells and which have in each case accumulated at a specific location in the immediate wound region of the traumatised skin, a corresponding use, where the topically and locally applied EPO causes no or substantially no stimulation of vascular or endothelial precursor cells circulating systemically in the bloodstream, a corresponding use, where the said cells stimulated by topically applied EPO express no or only a very small amount of CD31 antigen, a corresponding use, where the re-epithelialisation of the skin occurs 20 to 70%, preferably 20 to 50%, in particular 30-40%, more quickly than by EPO in an unstabilised form under otherwise identical conditions, a corresponding use, where the re-epithelialisation of the skin occurs 20 to 50%, preferably 30 to 40%, more quickly than by a corresponding pharmaceutical formulation without EPO under otherwise identical conditions, a corresponding use, where the topically and locally applied EPO stimulates the differentiation and growth of keratinocytes and/or hair root cells and/or connective-tissue cells, a corresponding use, where the topically and locally applied EPO additionally stimulates the differentiation and growth of CD90-positive and/or nestin-positive cells in the immediate wound region, a corresponding use, where the topically and locally applied EPO stimulates the differentiation and growth of nerve cells and/or neuronal precursor cells, a corresponding use, where corresponding precursor cells in deeper tissue layers in the local vicinity of the wound are stimulated by the topically and locally applied EPO.

One of the main problems in systemic administration of EPO is to achieve a sufficiently high tissue-protective action in regional areas while taking into account the systemic side effects on the one hand and the necessity for establishing a high active-compound concentration on the other hand.

The aim of the invention was therefore also to create an application method and a carrier material by means of which EPO and analogues thereof can be applied topically in a particularly effective manner.

Surprisingly, it has been found that the action effect described of topically applied EPO and derivatives and analogues thereof having the same biological action is particularly pronounced if the active compound is offered for topical application in a pharmaceutical preparation or formulation which stabilises it, where the formulation or preparation should have the further property that the active compound can be released to the wound as uniformly as possible and relatively slowly (slow release).

Surprisingly, it has been found that gel-forming, hydrophilic, relatively high-viscosity polymers, such as cellulose derivatives, carbomers, fatty alcohols or macrogols (polyethylene glycols) or mixtures thereof, preferably gel-forming polysaccharides, in particular from the group of the cellulose ethers and cellulose esters, as carrier substance or formulation base exert a stabilising action on EPO and derivatives thereof in corresponding EPO-containing preparations to be applied topically, such as ointments, creams, pastes or gels. The active compound here is uniformly distributed in a viscous, swollen, polymerised or gelatinous matrix, preferably polysaccharide matrix, which protects it and from which it is, in addition, released uniformly and slowly to the wound, in which it is able to develop its action directly and immediately without significant decomposition by proteolytic enzymes taking place.

Interestingly, EPO-containing gels having a relatively high viscosity of greater than 20,000 mPa s, preferably greater than 30,000 mPa s, in particular between 20,000 and 100,000 mPa s, preferably between 40,000 and 60,000 mPa s, exhibit more advantageous results than lower-viscosity gels having viscosity values of below 20,000 mPa s, in particular below 10,000 mPa s. Such viscosity values can be achieved in gels in which the gel-forming polymer, preferably the polysaccharide gel former, has a proportion of 2-4% by weight, preferably 2-3%, but not significantly less.

Gel formulations which comprise, as gel former, at least one swellable polysaccharide selected from the group consisting of hydroxymethylcellulose, hydroxyethylcellulose, carboxymethylcellulose and carboxyethylcellulose have proven particularly advantageous. Preference is given to formulations which comprise or consist of carboxymethylcellulose and/or hydroxyethylcellulose.

Besides gelatinous compositions based on polysaccharides, such as celluloses or also alginates, other swellable polymers having an overall hydrophilic action and the requisite viscous properties, as are used in many commercially available formulations, for example gels, pastes, ointments, are in principle also suitable.

It is also possible to use hydrophobic, polymeric, generally high-viscosity matrices, for example based on polyacrylates or polyurethanes, in which hydrocolloidal particles comprising polysaccharides, such as carboxymethyl/ethylcelluloses, gelatine or pectins, which comprise the active compound are embedded.

Figure 1:
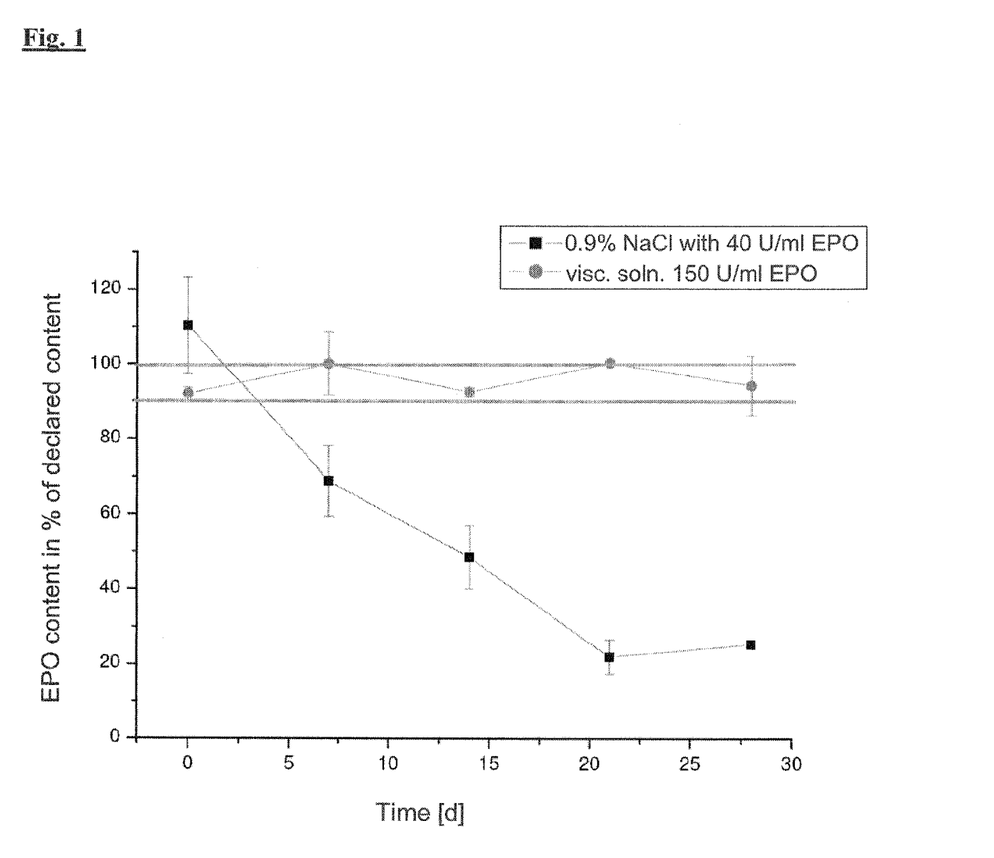
FIG. 1: Stability Study of EPO-Containing Preparations

The EPO is stable over a long period of more than 30 days in the advantageous gel formulations according to the invention (FIG. 1), while the EPO content in an aqueous EPO solution of comparable concentration (in 0.9% NaCl) has already dropped by 80% after 20 days.

By contrast, a wound which has been treated with an EPO-containing formulation according to the invention heals about 10-50%, preferably 20-40%, more quickly compared with a formulation according to the invention without EPO. Thus, for example, wound healing of between 92 and 99% can be achieved by re-epithelialisation after 4 to 8 days with an EPO-containing formulation according to the invention, whereas wound healing with the formulation according to the invention without EPO is only a maximum of up to 85-87% under otherwise identical conditions.

The invention thus relates to:
- a viscous formulation based on at least one gel-forming, hydrophilic polymer having a viscosity of at least 20,000 mPa×s, which comprises erythropoietin or one of its derivatives or analogues having the same biological action (EPO), and is capable of releasing the latter uniformly to a hydrophilic environment,
- a corresponding viscous formulation which has a viscosity of at least 30,000 mPa×s, preferably 40,000 to 60,000 mPa×s,
- a corresponding viscous formulation which preferably comprises, as hydrophilic polymer, a cellulose derivative, in particular a polysaccharide selected from the group of the hydroxyalkylcelluloses and/or carboxyalkylcelluloses, and a hydrophobic polymer matrix based on polyacrylate or polyurethane,
- a gelatinous or viscous formulation based on at least one swellable polysaccharide selected from the group of the hydroxyalkylcelluloses and/or carboxyalkylcelluloses, which comprises erythropoietin or one of its derivatives or analogues having the same biological action (EPO),
- a corresponding formulation which is obtainable by mixing EPO in lyophilised, dissolved or suspended form with the pre-swollen polysaccharide,
- a corresponding formulation in which the fully swollen polysaccharide has a viscosity of 5000-100,000 mPa×s, in particular 20,000-50,000 mPa×s,
- a corresponding formulation in which the polysaccharide(s) is (are) employed in a concentration of 0.4 to 4% by weight, in particular 2-3% by weight,
- a corresponding formulation in which the polysaccharide is a cellulose ether and/or a cellulose ester and is selected from one or more members of the group consisting of:
  hydroxyethylcellulose
  hydroxymethylcellulose
  carboxyethylcellulose
  carboxymethylcellulose
- a preferred formulation comprising, as gel former, polymerisable hydroxyethylcellulose and/or carboxymethylcellulose,
- a corresponding formulation which comprises EPO in a concentration of 100 to 500 IU/g of gel formulation, in particular 150 to 300 IU/g of gel formulation, preferably 150 IU/g of gel formulation,
- a corresponding formulation which comprises 0.5 g to 5 g of gel formulation/cm$^2$ of wound area, preferably 1 g to 3 g of gel formulation/cm$^2$ of wound area, in particular 1.0 g/cm$^2$ of wound area,
- a corresponding formulation which, depending on the amount of gel used, has an amount of EPO which would correspond, for a wound area of about 100 cm$^2$, to a systemic administration of about 50-2200 IU/kg of body weight (BW, for standard weight of 70 kg), or about 100-4500 IU/BW for a wound area of about 200 cm$^2$, and about 150-6000 IU/BW for a wound area of about 300 cm$^2$,
- a corresponding formulation which comprises, depending on the wound size or wound area (1 cm$^2$ to 300 cm$^2$), an amount of EPO of about 50 to about 450,000 IU, on average about 500 to 300,000 IU, preferably 1500 to 60,000 IU, in particular 3000 to 10,000 IU,
- a corresponding formulation which additionally comprises at least one further active compound, which preferably has an antibacterial, antiviral, fungicidal or antiinflammatory action, acts as proteinase inhibitor or is otherwise necessary for wound healing,
- a corresponding formulation which additionally comprises at least one synthetic copolymer,
- a corresponding formulation which additionally comprises one or more adjuvants,
- a corresponding formulation which has been introduced into or onto a solid carrier matrix which modulates the release of active compound and in particular releases the EPO uniformly into the wound region of the traumatised skin,
- a corresponding formulation in which the solid carrier matrix is a plaster, a foil, a film, a bandage, a gauze, but in particular a three-dimensionally structured plaster which is capable of stabilising and protecting the formulation itself, a pharmaceutical kit of parts, comprising at least two separate pack units, where the first unit comprises at least one swellable polymer and the second unit comprises lyophilised EPO or a corresponding derivative thereof.

The formulations according to the invention can be used for the topical and local treatment of injured skin and skin diseases of various cause in humans and animals. The formulations according to the invention can, in particular, also be used in dental medicine and/or for improving wound healing in general medicine or veterinary medicine. The formulations according to the invention can also be used in topical and local treatments of post-operative or post-traumatic wound infections and burns, in post-operative sepsis, in inflamed and/or infected ulcers, in chronic ischaemic wounds, in acute and chronic skin infections or dermatoses, in acne, rosacea, psoriasis or in mucous membrane ulcerations, or mucous membrane injuries, such as mucous membrane bone wounds, in particular in the jaw or dental area.

The invention thus also relates to the use of the formulation specified above and below for the preparation of a medicament for the topical and local treatment and healing of wounds by re-epithelialisation of the skin, in particular for the treatment and healing of burn wounds or of skin, mucous membrane and bone wounds and wounds in the dental area.

BRIEF DESCRIPTION OF THE DRAWINGS

As can be seen in FIG. 1, the EPO content varies in the range 90-100% of the nominal content (150 U/ml) during the investigation, meaning that the preparation and also the corresponding hydrogel can be assumed to be stable over a period of 4 weeks after preparation.

By contrast, a significant degradation of EPO was apparent in the sodium chloride-containing solution (0.9% by weight of NaCl in water comprising 40 U/ml of EPO) over the experiment period, meaning that only between 20 and 30% of the nominal content were found after three and four weeks.

FIG. 2:

The figure shows the re-epithelialisation of the skin, in %, of traumatised rats which had been treated with a formulation according to the invention (3% of carboxymethylcellulose) without EPO (control/placebo, gel F—left-hand bar) and with EPO (about 0.3 g of gel: 150 IU/g of gel=about 200 IU/BW, gel E—right-hand bar) for 4 days.

The results are shown in tabular form (top picture) and graphically (bottom picture).

FIG. 3:

The figure shows the re-epithelialisation of the skin, in %, of traumatised rats which had been treated with a formulation according to the invention (3% of carboxymethylcellulose) without EPO (control/placebo, gel F—left-hand bar) and with EPO (about 0.3 g of gel: 150 IU/g of gel=about 200 IU/BW, gel E—right-hand bar) for 8 days. The bandage/plaster was changed after four days, and the wound was treated with fresh gel. After treatment with the formulation according to the invention for 8 days, the skin is virtually 100% restored.

The results are depicted in tabular form (top picture) and graphically (bottom picture).

FIG. 4:

The results show that the layer thickness of the epithelium is significantly increased on treatment with EPO compared with the control formulation. In addition, it can be seen that neoformation of the epithelium is essentially not correlated with an increase in CD31-positive (stained) cells, but is to a certain extent with nestin-positive cells.

FIG. 5:

FIG. 6:

DETAILS OF THE INVENTION

Figure 4:
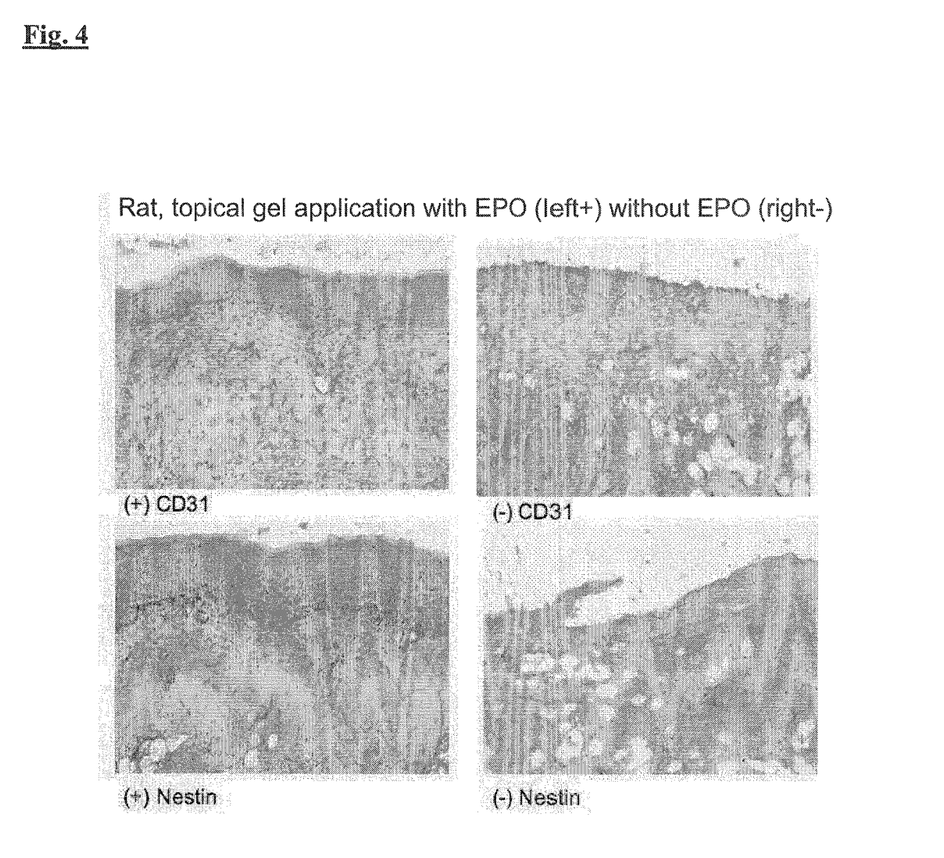
FIG. 4 depicts the histological investigation of wound healing after treatment with a gel as described in Example 8 for 8 days. Cells which express CD31 protein and nestin have been visualised by appropriate staining.

It has been found that rapid defect closure can be achieved in the case of skin regeneration, for example after burn trauma, scalding, or disease-induced wounds by topically applied EPO, in particular in the form of a gelatinous formulation described in greater detail above and below, in particular a hydrogel based on cellulose. Furthermore, re-epithelialisation of the wound region is crucially promoted by topically administered EPO. This is evident from a greater layer thickness of the epithelium (FIG. 4). This can only occur if the formation of the parenchymal components of the skin is also stimulated as rapidly as possible.

It can furthermore be observed that the formation of a vascular network is also initiated by topically applied EPO, but this is associated with local formation of the parenchyma, in contrast to the known teaching that wound healing caused by EPO is firstly set in motion by stimulation of vessel-forming cells, i.e. EPO merely causes vascular formation and the formation of parenchymal tissue commences indirectly and at best in a time-delayed manner, as a consequence of EPO stimulation of endothelial cells and precursor cells thereof.

However, the results of the present invention clearly show that the formation of vascular cells is coordinated at least at the same time with localised tissue formation.

It can furthermore be observed in accordance with the invention that the topical application of EPO causes tissue-specific precursor cells which are nestin-positive to be found to an increased extent in the boundary region of the new epidermis. Neuronal stem cells are thus stimulated in this region, which explains the improved sensitivity of the skin during wound healing.

For the formulations according to the invention, use is preferably made of recombinant erythropoietin, as is commercially available. However, it is also possible to employ in accordance with the invention EPO derivatives which have been developed in order to extend the half-value period of the active compound in the blood or in the serum compared with native EPO. EPO derivatives of this type can also be employed for topical application, although this is not absolutely necessary since the gelatinous formulations according to the invention develop their own specific protective action against normal EPO. These include, for example, pegylated EPO, EPO with a modified glycosylation pattern (for example Aranesp®), silylated EPO, or EPO which has been fused to other polypeptides or fragments of immunoglobulins (for example to the Fc part of an antibody) (known, for example, from WO 02/49673 or WO 01/02017). Furthermore, biologically active synthetic EPO peptide mimetics (as known, for example, from WO 96/40749, WO 96/40772, WO 01/38342, WO 01/091780, WO 2004/101611, WO 2004/100997, WO 2004/101600, WO 2004/101606 and WO 2006/050959) can also be employed. Since these mimetics usually have significantly shorter amino acid chains and thus generally undergo faster degradation, they experience the requisite and adequate stabilisation by the formulations according to the invention.

In the case of the known systemic use of EPO, between 150 and 300 IU/kg of body weight (BW) of the active compound are generally applied per dose. At significantly higher doses, the undesired side effects become dominant. In the case of an adult human (70 kg), this corresponds to between 10,500 and 31,500 IU of EPO/dose. This in turn corresponds to about 80 to 250 µg of EPO/dose (13,000 IU~100 µg of EPO).

In the case of the topical use according to the invention for injuries to the skin, significantly larger amounts of EPO can be employed per dose by means of the formulations or gels according to the invention without significant side effects occurring. Thus, for wounds of corresponding size (for example 300 cm$^2$), EPO amounts which would correspond to about 6500 IU/kg of body weight (BW) in the case of systemic administration can be employed. Such an amount of EPO applied systemically would no longer be tolerable. The requisite total amounts of EPO vary considerably depending on the wound size and amount of gel for a wound area and content of EPO/g of gel.

In general, the dose can be regarded in accordance with the invention as the amount of EPO which is required for single treatment of a wound (of various size). Since a wound is defined not only by its area, but also where appropriate by its depth, the dose of requisite active compound can vary greatly, since the wound is preferably filled with the formulation according to the invention.

If the body weight for an adult human is taken as 70 kg, the following values, for example, arise for wound healing:
50-500 IU/BW→3500-35,000 IU of EPO per dose or wound and wound size;
50-150 IU/BW→3500-10,500 IU of EPO per dose or wound and wound size;
100-500 IU/BW→7500-35,000 IU of EPO per dose or wound and wound size;
150-300 IU/BW→10,500-21,000 IU of EPO per dose or wound and wound size.
The wound sizes and gel concentrations that correspond to these values are shown in Table 1.

The low EPO units are preferably employed for small wounds having a wound area of about 5-20 cm$^2$, while the upper values are used for large wounds having an area of around 100 cm$^2$ or larger. In the case of wounds having an area of, for example, 10 cm$^2$, EPO amounts of between about 500 and 15,000 IU can be employed in accordance with the invention. In the case of wounds having an area of, for example, 100 cm$^2$, about 5000-150,000 IU of EPO are required. This means that on average about 50-1500 IU of EPO/cm$^2$ of wound area, preferably 75-450 IU of EPO/cm$^2$, should be applied in accordance with the invention to the wound for re-epithelialisation and defect closure of the wound. The amounts applied may of course be significantly above or below the said values under certain conditions.

The above-mentioned values are based on an EPO content of 100-500 IU/g of gel formulation, in particular 100-300 IU/g of gel formulation, preferably 150-200 IU/g of gel formulation. In detail, the following ranges of EPO amounts are employed in accordance with the invention per gram of formulation base:

100 IU/g of gel-300 IU/g of gel, 100 IU/g of gel-150 IU/g of gel,

100 IU/g of gel-200 IU/g of gel, 100 IU/g of gel-250 IU/g of gel,

150 IU/g of gel-200 IU/g of gel, 150 IU/g of gel-250 IU/g of gel,

150 IU/g of gel-300 IU/g of gel, 200 IU/g of gel-250 IU/g of gel,

250 IU/g of gel-300 IU/g of gel.

In general, about 0.5 to about 5 g, preferably 1-3 g, in particular 1 g, of gel according to the invention are used per square centimeter (cm$^2$) of wound area in an adult, depending on the injury. However, the amounts used may be above or below these concentrations. In particular, the following gel concentration ranges are employed: 0.5 g of gel/cm$^2$-2.0 g of gel/cm$^2$, 0.5 g of gel/cm$^2$-1.0 g of gel/cm$^2$, 1.0 g of gel/cm$^2$-2.0 g of gel/cm$^2$.

Formulations according to the invention thus comprise, for example, approximately the following amounts of EPO (IU) or the amounts of EPO indicated in Table 1 per dose, corresponding to the wound size and the amount of EPO per gram of formulation base: 2000 IU, 3000 IU, 4000 IU, 5000 IU, 6000 IU, 7000 IU, 8000 IU, 9000 IU, 10,000 IU, 12,000 IU, 15,000 IU, 20,000 IU, 25,000 IU, 30,000 IU, 35,000 IU, 40,000 IU, 45,000 IU, 55,000 IU, 60,000 IU, 70,000 IU, 80,000 IU, 90,000 IU, 100,000 IU, 120,000 IU, 135,000 IU, 150,000 IU and 180,000 IU.

TABLE 1

| cm$^2$ of wound area | Amount of gel (g) | IU of EPO (100 IU/g of gel) | IU of EPO (150 IU/g of gel) | IU of EPO (200 IU/g of gel) | IU of EPO (300 IU/g of gel) | IU of EPO (500 IU/g of gel) |
|---|---|---|---|---|---|---|
| (A) 0.5 g of gel/cm$^2$ of wound area | | | | | | |
| 1 | 0.5 | 50 | 75 | 100 | 150 | 250 |
| 10 | 5 | 500 | 750 | 1000 | 1500 | 2500 |
| 100 | 50 | 5000 | 7500 | 10,000 | 15,000 | 25,000 |
| 200 | 100 | 10,000 | 15,000 | 20,000 | 30,000 | 50,000 |
| 300 | 150 | 15,000 | 22,500 | 30,000 | 45,000 | 75,000 |
| (B) 1 g of gel/cm$^2$ of wound area | | | | | | |
| 1 | 1 | 100 | 150 | 200 | 300 | 500 |
| 10 | 10 | 1000 | 1500 | 2000 | 3000 | 5000 |
| 100 | 100 | 10,000 | 15,000 | 20,000 | 30,000 | 50,000 |

TABLE 1-continued

| cm² of wound area | Amount of gel (g) | IU of EPO (100 IU/g of gel) | IU of EPO (150 IU/g of gel) | IU of EPO (200 IU/g of gel) | IU of EPO (300 IU/g of gel) | IU of EPO (500 IU/g of gel) |
|---|---|---|---|---|---|---|
| 200 | 200 | 20,000 | 30,000 | 40,000 | 60,000 | 100,000 |
| 300 | 300 | 30,000 | 45,000 | 60,000 | 90,000 | 150,000 |
| (C) 2 g of gel/cm² of wound area | | | | | | |
| 1 | 2 | 200 | 300 | 400 | 600 | 1000 |
| 10 | 20 | 2000 | 3000 | 4000 | 6000 | 10,000 |
| 100 | 200 | 20,000 | 30,000 | 40,000 | 60,000 | 100,000 |
| 200 | 400 | 40,000 | 60,000 | 80,000 | 120,000 | 200,000 |
| 300 | 600 | 60,000 | 90,000 | 120,000 | 180,000 | 300,000 |
| (D) 3 g of gel/cm² of wound area | | | | | | |
| 1 | 3 | 300 | 450 | 600 | 900 | 1500 |
| 10 | 30 | 3000 | 4500 | 6000 | 9000 | 15,000 |
| 100 | 300 | 30,000 | 45,000 | 60,000 | 90,000 | 150,000 |
| 200 | 600 | 60,000 | 90,000 | 120,000 | 180,000 | 300,000 |
| 300 | 900 | 90,000 | 135,000 | 180,000 | 270,000 | 450,000 |

In accordance with the invention, the novel formulations comprise at least one gel-forming, viscous, hydrophilic polymer, preferably a cellulose derivative, preferably a polysaccharide, or alginates or derivatives thereof, chitin or derivatives thereof or salts thereof, or starch. The origin of the gel-forming polysaccharides is unimportant here, i.e. these gel-forming polysaccharides can be of vegetable or animal origin or prepared synthetically. It is also possible to use polysaccharides which are of vegetable or animal origin and have in addition been modified by chemical synthesis.

Cellulose derivatives are preferably employed for the gels or formulations according to the invention. The group of the cellulose derivatives in connection with the present invention includes, in particular, cellulose ethers and cellulose esters and salts thereof. Cellulose ethers used here are, in particular, hydroxyalkylcelluloses, such as, for example, hydroxymethylcellulose, hydroxyethylcellulose, hydroxypropylcellulose or hydroxybutylcellulose, but in particular hydroxymethylcellulose or hydroxyethylcellulose. Cellulose esters used here are, in particular, carboxyalkylcellulose, in particular carboxymethylcellulose, carboxyethylcellulose, carboxypropylcellulose or carboxybutylcellulose, but preferably carboxymethylcellulose or carboxyethylcellulose, where carboxymethylcellulose is the most preferred.

According to a further embodiment, the formulation according to the invention may also comprise at least two different gel-forming polysaccharides of those mentioned above, in particular of the cellulose derivatives mentioned above. It has proven particularly advantageous here for at least one compound from the class of the cellulose ethers and at least one compound from the class of the cellulose esters to be employed. Particular preference is given here to a formulation/hydrogel which comprises, as gel-forming polysaccharides, hydroxyalkylcellulose and carboxyalkylcellulose, in particular hydroxyethylcellulose and carboxymethylcellulose.

Furthermore, a gel according to the invention may in particular comprise, as gel-forming polysaccharide, at least one water-soluble cellulose derivative. These are distinguished by the fact that they do not form swollen particles within the gel, in turn resulting in a very homogeneous hydrogel. In addition, a water-soluble polysaccharide-containing gel exhibits particularly good spreadability on application to a wound, in addition forms a particularly smooth surface and can be modelled particularly well. Water-soluble cellulose derivatives which are not crosslinked are particularly suitable here.

The formulations according to the invention may furthermore comprise a structure former or a viscosity-modulating compound. Polyacrylic acid and salts thereof and in particular crosslinked polyacrylates are particularly suitable for this purpose. Examples of suitable acrylates of this type are: (poly)methacrylate, (poly)methyl methacrylate, polyacrylamide, (poly)ethoxyethyl methacrylate. These polyacrylic acid derivatives additionally have the advantage that they are able to take up a considerable proportion of their own weight in water. The combination of these acrylic acid derivatives with at least one gel-forming polysaccharide thus enables the specific preparation of a gel whose water uptake and water release capacity can be controlled. The ratio between cellulose derivative and acrylic acid derivative in the formulation can be between 20:1 and 1:1, but preferably between 10:1 and 2:1.

Furthermore, the formulation according to the invention can be based on a viscous polymer which overall has a hydrophilic action and which has a hydrophobic carrier or supporting matrix, for example comprising polyurethane or polyacrylate, in which said polysaccharides comprising the active compound, such as, for example, carboxyalkylcelluloses, are embedded. Hydrogels of this type are particularly suitable for wound healing since they keep the wound moist, create an optimum environment for autolytic debridement, and deposit wound secretions in the secondary bandage. An example thereof is Varihesive® hydrogel.

In general, other hydrophobic polymer backbones or supporting structures in which hydrocolloidal particles of a polysaccharide, as indicated above, are embedded are also possible.

In principle, all gel and ointment bases based on polymers, in particular built up on the basis of polysaccharides, and which have proven particularly suitable for wound healing and are commercially available are suitable for the formulation according to the invention so long as uniform slow release of EPO by maintenance of viscosity values as described above and below is ensured.

The formulations according to the invention may furthermore additionally comprise electrolytes. Suitable electrolytes in connection with the present invention are compounds which are capable of dissociation into ions, in particular on dissolution in water, and are built up from mono-, di- and/or trivalent ions. These electrolytes can be, for example, in the form of inorganic or organic salts and differ from any polymers having an ionic character which may be present in the formulation. Particularly suitable in this connection are chlorides, iodides, sulphates, hydrogensulphates, carbonates, hydrogencarbonates, phosphates, dihydrogenphosphates or hydrogenphosphates of the alkali and alkaline-earth metals, but in particular sodium chloride, potassium chloride and calcium chloride. These electrolyte mixtures simulate particularly well the electrolyte mixture in a wound serum released by a wound. These electrolyte-containing formulations according to the invention thus provide the wound with a sphere which promotes wound healing to a particular extent.

In a further alternative embodiment of the invention, the formulation according to the invention additionally comprises a polyol. This polyol is highly suitable as moisture donor and thus represents a care component for the skin surrounding the wound. Particularly suitable for this purpose are polyols which can be selected, for example, from the group consisting of: glycerin (glycerol), glycol, propylene glycol, polyethylene glycol, polypropylene glycol, polyethylene-propylene glycol or mixtures thereof. In particular, the polyol employed in the present hydrogel can be glycerin or polyethylene glycol and mixtures thereof in amounts of between 0.5% and 10% (w/w), based on the entire gel.

The formulations or gels, in particular hydrogels, according to the invention must have a viscosity which is suitable for protecting EPO in an optimum manner, but at the same time ensure that the active compound can be released to the wound in sufficient amount and sufficiently quickly without previously being metabolised.

Surprisingly, it has been found that this is ensured in an optimum manner only by means of formulations which have a relatively high viscosity, which is achieved with a proportion by weight of swellable polymer in the gel as a whole, preferably of cellulose derivatives, of at least 1.5%, but preferably 2-4%, very particularly preferably 2.5-3.5%, in particular 3% or around 3%. Gels having such a viscosity are generally rarely employed for medical purposes, since they usually cannot be processed as well as gels having a gel former content of 1-2%. As mentioned above, the use of, for example, acrylates enables the processability of the gel to be improved.

The gels or formulations according to the invention based on hydrophilic polymers, such as, for example, cellulose ethers and/or cellulose esters, for example carboxyalkylcelluloses, thus have a dynamic viscosity of 5000 to 100,000 mPa s, preferably greater than 20,000 mPa s, in particular 20,000 to 70,000 mPa s and very particularly 40,000 to 60,000 mPa s (measured in Bohlin model CSR—10 rheometer, 4°/0.40 mm conical spindle, oscillometric measurement, T=22-25° C.). A hydrogel of this type can be distributed sufficiently well and uniformly over and in a wound, has good coherence even on uptake of wound exudate and does not run out of a wound to be treated.

It is provided that the preferred EPO-containing formulations or gels according to the invention have the following composition: at least 70% by weight of water and 1.5-6.0% by weight of gel-forming polysaccharide, preferably at least one cellulose derivative, in particular carboxymethylcellulose and/or hydroxyethylcellulose, and optionally 0.1-10% by weight of acrylic acid derivative and/or 1-20% of polyol, preferably 1-5% by weight of glycerol, and/or 0.1-5% by weight of electrolyte.

The formulations according to the invention may optionally comprise adjuvants known per se for the gel preparation, including suitable preservatives.

The formulations or gels according to the invention may also comprise other active compounds which are necessary as such for wound healing. This is particularly appropriate if, for example, bacterial, viral or fungal infections have occurred or prophylaxis against such infections is intended. Corresponding antibiotics, antimycotics or also antiphlogistics which are suitable for this purpose are described in the prior art. In particular, active compounds which can be employed topically are suitable here. Examples of antibiotics which can be employed topically are tetracyclins or penicillins or also erythromycin, bacitracin, tyrothricin, colistin and polymyxin B or aminoglycosides, such as neomycin, kanamycin and paromycin or mupirocin.

In a particular embodiment, at least one proteinase inhibitor, which is intended to inhibit the proteinases which occur to a massive extent in the wound secretion, is added to the formulation according to the invention. A particularly suitable proteinase inhibitor in accordance with the invention is aprotinin, which is capable of inhibiting the pro-inflammatory cytokine secretion which occurs in a wound. Surprisingly, it has been found that EPO is particularly effective for wound healing on topical administration in the presence of aprotinin.

Furthermore, the gels or formulations according to the invention may also comprise disinfectants, such as, for example, povidone-iodine or the like.

Besides the EPO-containing formulation according to the invention as such, the present invention also relates to a wound dressing which comprises a medical carrier material and the formulation or gel of the type described. For example, the carrier material employed here comprises nonwovens or knitted or woven textile fabrics made from natural or synthetic fibre materials, but also film coverings, for example in the form of a spray plaster. The medical carrier material here is coated or impregnated with the gel or hydrogel on one or more sides.

A very particularly suitable wound dressing can be provided in the form of a special plaster which comprises the active compound EPO in a particularly optimised manner and releases it to the wound.

A plaster of this type is described in detail in EP 08 011 985.2 and comprises a carrier matrix which comprises the active compound(s), where the carrier matrix has the following to structure:
(i) areas or structures in the form of one or more cavities serving as container for the medicament, and (ii) areas or structures in the form of one or more cavities serving as channel-like structures, which serve for the uptake and draining of wound secretions and/or aeration and/or topical introduction of further active compounds and/or of cells which promote skin healing, where (a) at least one area in accordance with (i) is adjacent to at least one area in accordance with (ii), (b) areas (i) and (ii) are sealed on the side facing away from the wound, (c) areas (i) and (ii) are open or at least permeable to the active compounds, wound secretions, further active compounds/said cells on the side facing the wound, (d) the areas (i) and (ii) in the form of cavities are arranged in the plane of the plaster surface, and (e) the cavities in areas (ii) have at least one opening or connection for a syringe or suction/supply device which enables either the drainage of wound secretions which have accumulated in the cavities, with generation of a reduced pressure in the plaster, and/or optionally the application of said further active compounds.

A corresponding EPO-containing plaster may furthermore be designed in such a way that, in the case of weeping skin or wounds or skin or wounds which produce wound secretions, (f) the cavities in areas (ii) additionally have drainage means which enable wound secretions which have accumulated in the cavities to be drained. In this case, the cavities in areas (ii)

may be channels which are connected to one another. The cavities in areas (i) may be trough-shaped, where the open side of the troughs faces the wound, and the troughs have a rectangular, square, hexagonal/honeycomb-shaped or round base area. The said cavities in areas (i) are separated from one another by bridges of the material of the carrier matrix. The bridges themselves may likewise have channel-like structures, at least some of which are connected to one another and which serve for the drainage of wound secretions and/or aeration and/or the supply of further active compounds/said cells.

In addition, the cavities in areas (i) serving as depot for the medicament represent sub-structures arranged in clusters, which are separated from one another by bridges of the material of the carrier matrix. The cluster domains have any desired rectangular, square, hexagonal/honeycomb-shaped or round base area shape, in particular a square or rectangular base area shape, where the shape of the cluster base area may, if desired, be identical to or different from the base area shape of the sub-structures of areas (i). It may be provided here that a cluster domain of area (i) is adjacent to at least one cavity of area (ii) and that, if desired, two cluster domains of areas (i) are separated from one another by a cavity of area (ii).

The formulations/gels according to the invention, which are optionally applied to a wound dressing which is known in principle and is commercially available, or, for example, like the plaster described above, can be changed every 12, 24, 48 or 72 hours, preferably every 48 hours, which may principally be necessary due to other factors and circumstances, such as, for example, the formation of wound secretions, bleeding or infections arising, which have to be treated. Merely for reasons of stability and activity of the active compound EPO within the formulation base according to the invention, however, it is not necessary to change the bandage or plaster before complete wound healing.

The gels according to the invention can be prepared by methods known per se. One of these methods is described in greater detail in the examples.

The EPO-containing gels according to the invention can, as indicated above, be employed, in particular, in the treatment of wounds, in particular to the skin, the mucous membrane, in the dental area, in the case of mucous membrane/jaw injuries in the oral cavity, or in the case of burns or scalds of the skin or skin diseases accompanied by chronic wounds. Wounds to the skin may be caused, for example, by cuts, punctures, crushing, bites or shot injuries, or may arise as an unavoidable consequence of operations or tooth extractions. Furthermore, diverse diseases may cause wounds to the skin or flesh, or form open ulcers. Relatively large wounds also arise in the case of organ transplants or amputations and have to be provided with therapeutic care topically and locally.

In the dental area, relatively small wounds may also arise in the case of carious inflammation and periodontitis and can successfully be treated with the formulations/gels according to the invention. If the enamel surface of the tooth is damaged, bacteria penetrate further into the underlying dentine. Pulp processes are present in the radial dentine tubules, meaning that partial or total infection and thus inflammation of the pulp then occurs. If no treatment is given, the consequence is death of the pulp tissue (necrosis) and bacterial decay (gangrene). If the gangrenous masses are not removed, inflammation outside the root tip is the consequence. Granulomas, cysts, fistula formation or abscesses may develop. EPO or the EPO-containing gel can successfully be employed at each of these stages, advantageously after corresponding antibacterial treatment.

The formulations or EPO-containing gels according to the invention are particularly suitable for the treatment of comparatively deep wounds and can be employed extremely well as wound fillers. Thus, for example, deep dermal ulcers, which very frequently weep heavily, can be treated with the gels according to the invention. The relatively high viscosity of the gel prevents liquid from trickling out of the wound, or at least reduces this. In addition, however, dry wounds, such as, for example, dry ulcus cruris, can also be treated with the present gel. In this case, the present gel exhibits its ability to supply the wound with liquid and to ensure the removal of undesired substances, deposits and necroses by gentle debridement. Other types of wound for which the formulation according to the invention can be used include, but are not limited to, stage I, II, III decubitus ulcers (pressure sores), ulcus cruris (leg ulcer, leg sore), diabetic foot syndrome, skin ulcers, blood ulcers, first and second degree burns, grazes and chronic wounds.

Finally, the invention relates to a kit of parts which comprises at least two separate packs, where the first pack comprises the materials of the hydrogel or constituents of the hydrogel, such as polysaccharide and/or polymeric (hydrophobic) supporting matrix, and the second pack comprises the active compound EPO as stable lyophilisate. The kit of parts may also comprise the constituents of the formulation base, if appropriate, in different packs. A pack containing an aqueous component matched to the amount, in which the solid components can be dissolved or suspended, may likewise be a further constituent of the kit of parts according to the invention, i.e. the pharmaceutical kit may include a further pack unit which comprises the solvent necessary for swelling/polymerisation (preferably water or water-containing agents). The kit according to the invention may comprise the swellable polymer in the form of a powder or in pre-swollen form, where, in the latter case, the viscosity of the pre-swollen polymer should be kept sufficiently low (preferably below 5000 mPa s) that uniform mixing with the active compound EPO from the second pack unit is ensured. After addition of EPO, the carrier polymer/gel can finally swell to completion with the desired viscosity.

The individual separated packs may also be physically connected to one another in such a way that their contents can be mixed with one another by simple mechanisms, such as piercing, puncturing, forcing through, tearing off or the like, for example in the form of a mixed closure system. In this way, it is possible to delay addition, in particular, of the active compound EPO, which has a very long shelf life in lyophilised form with retention of its activity, to the still not fully polymerised gel or formulation base until preparation of a fresh gel in the pre-swollen state of low viscosity in accordance with the invention immediately before application to the wound, meaning that losses of activity cannot occur, as may be the case under certain circumstances in active compound-containing formulations which are completely finished from the beginning.

The following examples are intended to describe the invention in greater detail, but without restricting it in any way. In particular, the person skilled in the art will be able, if desired, to generalise the knowledge from these examples with the aid of his general knowledge.

Furthermore, the substances indicated in the examples, including their parameters, properties, physical quantities, data, and the specific methods described, which the person skilled in the art, unless stated otherwise or prevented by sensible or technical/scientific reasons, will also be able to generalise and bring into other connections than indicated in the examples, should merely be regarded as illustrative.

EXAMPLES

Example 1

Erythropoietin (EPO) is used in the form of the finished medicament (NeoRecormon 10,000 TU, powder and solvent for the preparation of an injection solution in cartridges, batch MH68260 08, PZN 742 914 3, Roche Reg. Ltd., Welwyn Garden City, UK).

The active compound is converted into a pre-sterilisable preparation under aseptic conditions using the following gel formers:

Hydroxyethylcellulose Ph. Eur. 5.1 (trade name: Hydroxyethylcellulose 250 HX Pharm, batch 06E29-N01, Fagron, D-Barsbüttel)

Carmellose-sodium/carboxymethylcellulose Ph. Eur. 5.0 (trade name Tylopur C600, batch 516 762 65, Caelo, D-Hilden)

Methylcellulose/hydroxypropylmethylcellulose USP (trade name Metolose 90 SH-100, batch 206314, Shin-Etsu, D-Mülheim)

Povidon Ph. Eur. 5.0 (trade name Kollidön 25, batch 74-0915, BASF, D-Ludwigshafen)

Varihesive®, Convatec, Varihesive E® is a hydrocolloid bandage. It consists internally (lying on the wound) of a hydrocolloid layer based on a swellable polysaccharide which is embedded in an adhesive polymer matrix, and externally of a film-coated polyurethane foam.

Besides water for injection purposes as bulk (Ph. Eur. 5.0), glycerol (85% or anhydrous, batch 058 006 2, Fisher Scientific, Loughborough, UK) is used as adjuvant. The primary packaging employed for accommodation of the formulations is Fiolax injection vials, glass type I (Münner-städter Glaswarenfabrik GmbH, D-Münnerstadt). These are covered with 20 mm Pharma-Fix sealing discs and crimp-sealed with 21 mm metal crimp seals (both VWR, D-Hannover). The release studies are carried out using organotypical skin models, whose production, cultivation and use were carried out in accordance with the following reference: C. Hoffmann, C. C. Müller-Goymann, "*Use of artificial skin constructs in permeation studies of clindamycin phosphate*", Pharmazie 60 (2005) 350-353.

Example 2

Formulation of Hydrogels Containing No Active Compound

The gel former to be investigated is weighed out into a tared mortar under low-germ conditions and ground with the intended amount of glycerol. After addition of water for injection purposes as bulk in portions, the preparation is allowed to swell for at least 2 hours, before evaporated water is replaced and the hydrogel is homogenised in the mortar. The hydrogel is transferred into an injection vial which has been sterilised with hot air in 3.3 g portions, which can be carried out, depending on the consistency of the preparation, by drawing up by means of a syringe or by transfer into an Unguator jar and subsequent dispensing with the aid of an attached Unguator applicator (both Gako Konietzko GmbH, D-Bamberg). The sealed injection vial is then sterilised by means of saturated, live steam under standard conditions of Ph. Eur.

Example 3

Evaluation of the Rheological Properties of the Hydrogels Containing No Active Compound In order to be able to estimate the thermal degradation of the gel formers during autoclaving, sterilised hydrogels are assessed visually with unsterilised samples and measured in a plate-and-cone viscometer (GVO rheometer, Bohlin Instruments, Cirencester, GB) at a temperature of 20.0° C. and a cone apex angle of 1°. The final gel former content is defined in accordance with the therapeutic demands made of the formulation.

Example 4

Preparation of an EPO-Containing Gelatinous Formulation

In each case, 500 IU of EPO are injected into the cooled and pre-sterilised hydrogel from the reconstituted EPO 10,000 IU solution under a clean bench; to this end, use is made of a Reco-Pen (Roche Diagnostics GmbH, D-Mannheim), which releases the requisite medicament solution via an attached 12 mm Clickfine universal needle (Ypsomed, D-Sulzbach). Taking into account the EPO volume of 50 µl transferred for 500 IU of EPO, an active-compound content of 150 IU/g is obtained in the preparation. In order to be able to ensure homogeneous distribution with exclusion of the risk of protein denaturing, the EPO solution was allowed to diffuse into the hydrogel over 24 hours. For improved mixing, the injection vial was rotated twice through 180° in this period. The preparations were stored at +2 to +8° C. with protection against light. In detail, the following preparation procedure is used by way of example for a hydrogel having an erythropoietin content of 150 IU/g of gel:

Preparation of the gel containing no active compound under low-germ conditions

Grind carboxymethylcellulose 250 HX with glycerol (2.4%) in a mortar

Incorporate water in portions

Allow to swell for at least 2 hours

Replace evaporated water, homogenise. Alternatively, an electronic stirring system (e.g. Cito-Unguator 2000) can also be employed for the preparation of the gel containing no active compound Transfer gels in portions of 3.3 g each into an injection vial of glass type 1 which has previously been cleaned and sterilised with hot air, and crimp-seal, e.g. using a syringe or Unguator® applicator Autoclave crimp-sealed gel under standard conditions Bring injection vials to a temperature of +2 to +8° C. before further processing Transfer 500 IU of EPO into each injection vial under a clean bench, e.g. from NeoRecormon 10,000 E two-chamber cartridges using the Reco-Pen with release of 2 pen units via a Clickfine universal needle Allow EPO to diffuse in over at least 24 h, rotate the gel twice through 180° in the injection vial during this period for better mixing.

Gels are prepared analogously using hydroxyethylcellulose, carboxyethylcellulose, carboxypropylcellulose, hydroxypropylcellulose (between 1.5% and 3.5% (w/w) cellulose content).

Example 5

Stability Testing of EPO-Containing Formulations

In order to test the stability of erythropoietin in preparations, samples are taken at time 0, 1, 2, 3 and 4 weeks after preparation of the respective preparations and sent for erythropoietin analysis. Throughout the experiment period, the storage conditions mentioned above are maintained. In addition, a preparation having an erythropoietin content of 40 IU/ml in 0.9% aqueous sodium chloride solution is also included in the study. The results are shown graphically in FIG. 1.

Example 6

Active Compound Release Experiments Through Skin Constructs

The release experiments are carried out using six Franz cells (volume: 5.68-8.88 cm$^3$, permeation area: 0.14-0.34 cm$^2$) which contain an isotonic glycerol solution held at 37° C. in the acceptor compartment. The organotypical skin construct, which is mechanically stabilised against the acceptor solution in a downward direction by a polycarbonate filter and is in contact with the preparation to be tested in the upward direction, is introduced between the donor and acceptor compartments. Samples are taken after 0; 0.5; 1; 1.5; 2; 3; 4; 5; 6 and 24 hours with replacement of the acceptor volume of 1.0 ml removed and sent for erythropoietin analysis. A contact time of about 5 minutes, which is used for assembly of the cell, introduction of the acceptor and weighing, should be set for the period between the first contact of skin construct with the preparation to be tested and the first sampling (0 h). Four of the release cells mentioned above are used in order to test the formulation which, on the basis of formulation and stability studies, can be regarded as the most promising formulation. In order to obtain information on whether degradation of the medicament is to be feared during the release testing owing to the elevated temperature above the storage conditions, two further cells are charged with a viscous solution (erythropoietin content: 150 IU/g of hydrogel) in order to be able to determine the content from these solutions after completion of the release experiments.

Example 7

EPO Analysis

Since in all cases the amounts of medicament to be determined are too small to carry out quantification of the non-denatured and non-degraded erythropoietin content by means of optical circular dichroism, erythropoietin is determined by means of a sandwich ELISA with compliance with the manufacturer's instructions (EPO-ELISA, OSTEOmedical GmbH, D-Bünde). The measurement of the ELISA assay developed is carried out using a KC4 multiplate reader (Bio-Tek, D-Bad Friedrichshall) with software version 3.4 Rev 21. Since the contents of the administration forms prepared are above the quantification range of the assay, the respective samples are diluted before measurement in order to obtain a nominal content in the region of 400 mIU/ml. Samples from the release investigations can be measured without an interim dilution step.

Example 8

Skin Regeneration in Traumatised Rats Using a Carboxymethylcellulose Gel

Figure 2:
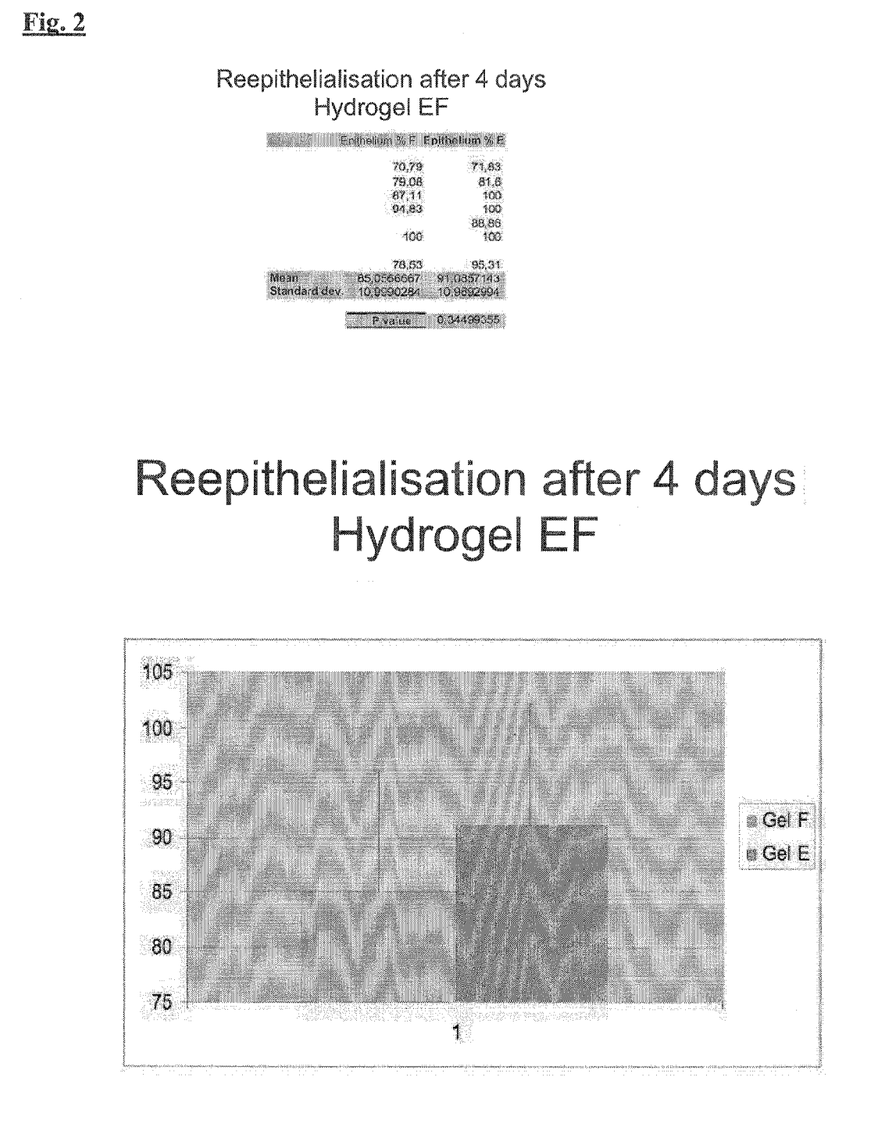
Figure 3:
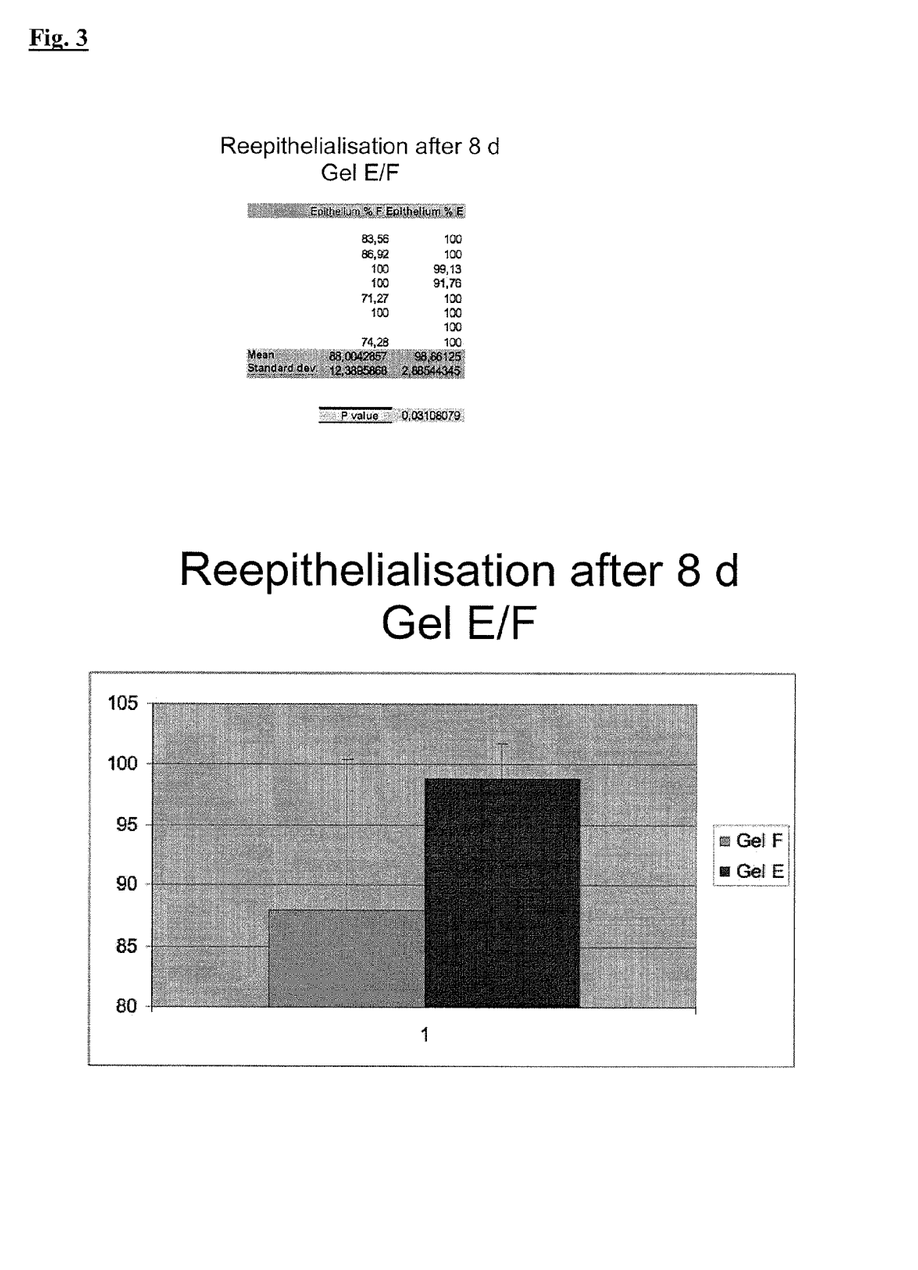

A tangential excision trauma is made in four female rats having a body weight of 200-250 g. The animals are treated with a gel prepared in accordance with the above details which comprises, as gel former, carboxymethylcellulose (3% (w/w), 42,000 mPa s) (furthermore 2.4% of glycerol) and 150 IU of EPO/BW. The controls (placebo) comprise no active compound. After application of the gel, the animals are provided with a bandage or plaster. The bandage/plaster is changed every 48 h. Tissue samples are taken from the wound region after 4 and 8 days and analysed histologically. Tests are carried out here for CD31- and nestin-positive or -negative cells by means of staining techniques known in the prior art. The results are shown in FIGS. 2, 3 and 4. It can be seen that the re-epithelialisation is completed significantly more quickly in the EPO-containing gels ("gel E", FIGS. 2 and 3) (on average 10-50%) than in the formulations containing no active compound ("gel F", FIGS. 2 and 3), depending on the duration of the treatment. In addition, it can be seen that, through cell-specific staining, neoformation of the epithelium generates essentially no new CD31-positive cells (FIG. 4).

Skin regeneration is investigated analogously in a 1% carboxymethylcellulose gel. The results are about 5-10% worse in the case of the EPO-containing gel formulation than in the case of a comparable 3% gel, while no significant differences are observed in the controls.

Skin regeneration is investigated analogously in a 1% gel and a 3% gel based on hydroxyethylcellulose with the same EPO concentrations. Comparable or only slightly worse results are obtained compared with the carboxymethylcellulose gel.

Example 9

The following gel formulation for treatment of a burn wound (about 120 cm$^2$) in an adult patient was prepared by the above-mentioned process:

| Constituent | % by weight |
|---|---|
| Hydroxyethylcellulose 250 HX Pharm | 3 |
| Glycerol (anhydrous) | 2.4 |
| Water (for injection purposes) | 94.6 |

100 g of a gel of this type were applied and comprised 12,000 IU of EPO and had a viscosity of about 40,000 mPa × s.

Example 10

The following gel formulation for treatment of a cut wound (2 cm$^2$) in an adult patient was prepared by the above-mentioned process:

| Constituent | % by weight |
|---|---|
| Hydroxyethylcellulose 250 HX Pharm | 4 |
| Glycerol (anhydrous) | 2.5 |
| Polyacrylate | 1.5 |
| Water (for injection purposes) | 92.0 |

2 g of a gel of this type were applied and comprised 1000 IU of EPO. Viscosity: about 68,000 mPa × s.

Example 11

The following gel formulation for treatment of a burn wound (about 300 cm$^2$) in an adult patient was prepared by the above-mentioned process:

| Constituent | % by weight |
|---|---|
| Hydroxyethylcellulose 250 HX Pharm | 2.5 |
| Glycerol (anhydrous) | 2.5 |
| Polyacrylate | 2.0 |
| Water (for injection purposes) | 93.0 |

450 g of a gel of this type comprised 50,500 IU of EPO and were distributed on the burn wound for treatment. Viscosity: about 35,000 mPa × s.

Example 12

The following gel formulation for treatment of a burn wound (80 cm²) in an adult patient was prepared by the above-mentioned process:

| Constituent | % by weight |
| --- | --- |
| Carboxymethylcellulose 250 HX Pharm | 3.5 |
| Glycerol (anhydrous) | 3.5 |
| Water (for injection purposes) | 92.0 |

50 g of a gel of this type were applied and comprised 35,000 IU of EPO. Viscosity: about 55,000 mPa × s.

Example 13

The following gel formulation for treatment of an open leg ulcer (150 cm²) in an adult patient was prepared by the above-mentioned process:

| Constituent | % by weight |
| --- | --- |
| Carboxymethylcellulose 250 HX Pharm | 3.0 |
| Glycerol (anhydrous) | 2.5 |
| Polymethacrylate | 1.0 |
| Water (for injection purposes) | 93.0 |

150 g of a gel of this type were applied and comprised 20,100 IU of EPO. Viscosity: about 49,000 mPa × s.

Example 14

The following gel formulation for treatment of a relatively large mucous membrane/jaw wound (1 cm²) as a consequence of a tooth extraction in an adult patient was prepared by the above-mentioned process:

| Constituent | % by weight |
| --- | --- |
| Carboxymethylcellulose A380 Aquasorb | 3.0 |
| Glycerol (anhydrous) | 2.5 |
| Water (for injection purposes) | 94.5 |

1 g of a gel of this type was applied and comprised 1500 IU of EPO.

Example 15

The following gel formulation for treatment of a relatively large mucous membrane/jaw wound (about 10 cm²) as a consequence of a tooth extraction in an adult patient was prepared by the above-mentioned process:

| Constituent | % by weight |
| --- | --- |
| Carboxymethylcellulose A380 Aquasorb | 2.0 |
| Hydroxyethylcellulose 250 HX Pharm | 1.0 |
| Glycerol (anhydrous) | 2.0 |
| Water (for injection purposes) | 95.0 |

30 g of a gel of this type were applied and comprised 20,500 IU of EPO. Viscosity: about 23,000 mPa × s.

Example 16

Chronic Ischaemic Wounds

Chronic ischaemic wounds are amongst the most common surgical clinical pictures in Germany alone and require intensive interdisciplinary treatment. In Germany, more than 3 million people suffer from chronic wounds, which can generally be divided into three types of wound: ulcus cruris, diabetic foot and decubitus. The costs for the treatment of chronic wounds in this country are currently running at about 5 billion euros per year.

The combination of an arterial ulcer (peripheral arterial occlusive disease) and a diabetic ulcer is regarded as particularly difficult to treat clinically and unfortunately is not rare.

Figure 5:
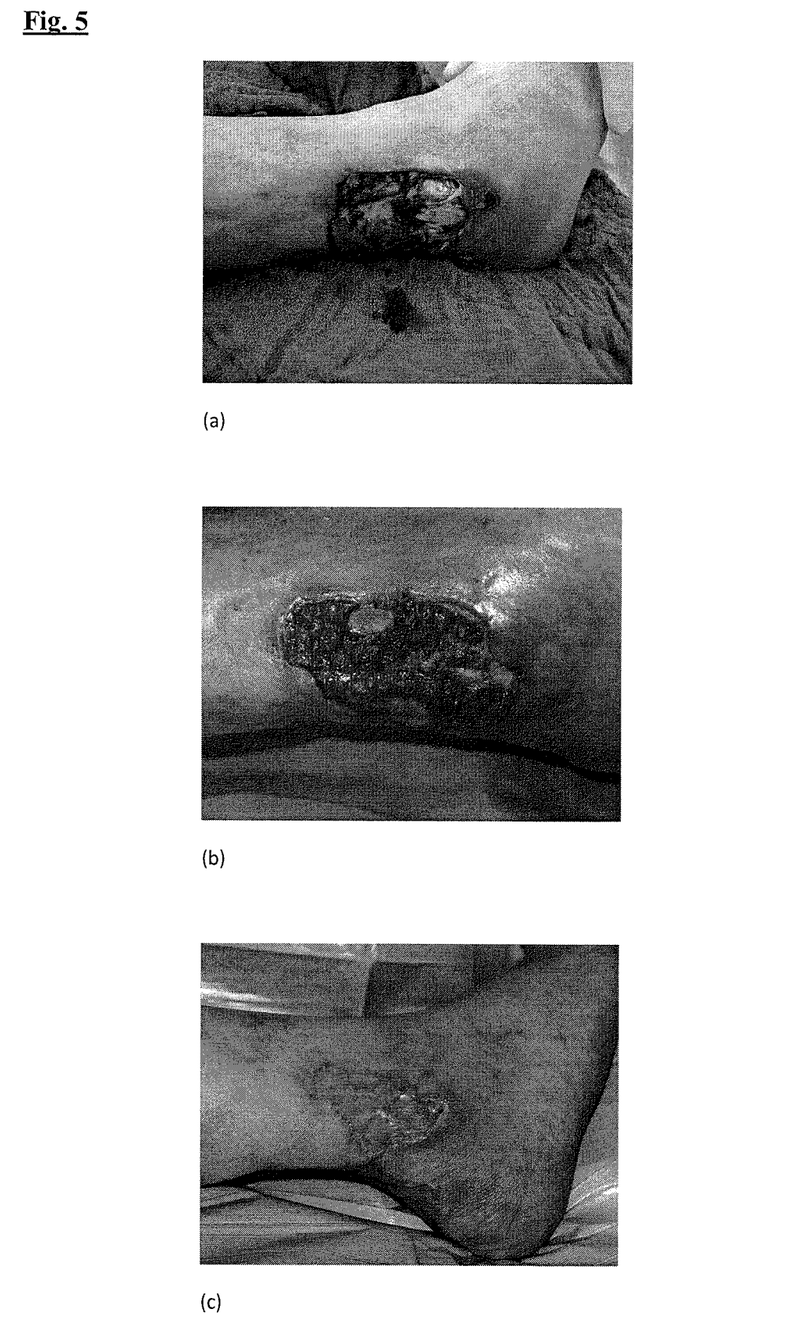
FIG. 5 is the photographic evidence of the healing of a third degree chronic ischaemic ulcer of the lateral malleolus in a diabetic patient after local treatment three times with the formulation according to the invention comprising 3000 IU of EPO (in total 9000 IU). The bottom picture shows the course after 15 days (Example 16).

A 69-year-old diabetic patient with grade IV pAVK has been suffering from a grade III chronic ischaemic ulcer of the lateral malleolus for more than 12 months (FIG. 5, top picture). After three local treatments with recombinant EPO (in each case 3000 IU) in Varihesive E® hydrogel having a correspondingly high viscosity, obvious formation of granulation tissue occurs (middle picture). Complete healing of the wound can be observed after 15 days after a subsequent split-skin graft (bottom picture).

Example 17

Dermal Wounds

Everyone will suffer from a certain number of mechanical or thermal dermal injuries which require healing in the course of his or her life. The market for local wound therapeutic agents in the form of liquids, ointments or bandage materials is correspondingly large. In the evidence-based analysis of affected patients, the fact that each skin wound has a different configuration is problematical. However, in surgery there is a highly standardised skin wound which is produced by the need to remove a part of the skin of defined thickness (usually 0.2 to 0.3 mm) using a special instrument (dermatome) in order then to graft it to another site in the body. Split-skin removal sites of this type (0.3 mm) usually heal without consequences within 10-14 days.

Figure 6:
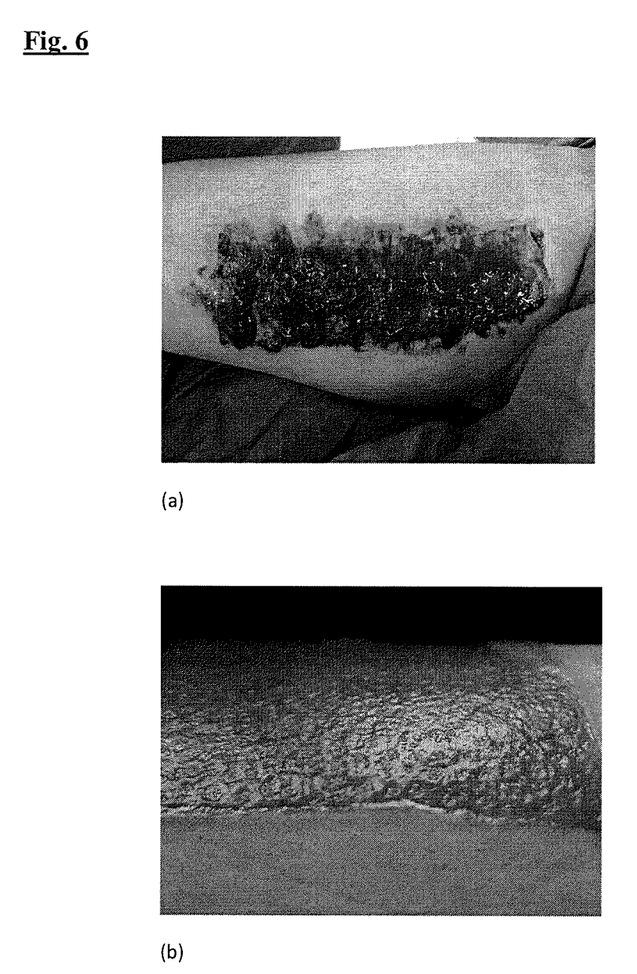
FIG. 6 shows a photograph of the healing process of a thermal wound after removal of a split-skin graft in a patient by treatment with a single administration of 3000 IU of EPO in a hydrogel according to the invention (Example 17).

A 25-year-old patient had a thermal injury whose treatment made split-skin removal necessary (FIG. 6, left-hand picture). The removal sites were treated with 1×3000 IU of EPO in hydrogel in accordance with one of the compositions indicated above (3% of carboxymethylcellulose). Complete healing was observed after only 7 days (FIG. 6, right-hand picture).

Similar results were achieved with four further patients who had suffered burns.

The therapy trial of split-skin graft removal sites with locally applied erythropoietin was carried out as follows on the said five patients: the split-skin grafts were each taken from the thigh with a thickness of 0.3 mm. The erythropoietin was mixed intraoperatively with Varihesive® hydrogel, which functioned as carrier substance, and applied directly to the wound. The wound area was subsequently covered with a perforated polyurethane film and a secondary bandage. The secondary bandage was only removed in the case of further local erythropoietin applications. The latter were carried out in a sterile manner, at a number of points, through the polyurethane film. The polyurethane film was only removed, atraumatically, seven days after the operation in order to assess re-epithelialisation.

The invention claimed is:

1. A gelatinous formulation for the topical treatment of a wound region of traumatized skin, comprising gel-forming swellable polysaccharides selected from the group consisting of:
   hydroxyethylcellulose in a concentration of 2-4% by weight and carboxymethylcellulose in a concentration of 2-4% by weight, and wherein the gelatinous formulation when fully swollen (i) has a viscosity of 40,000-60,000 mPa×s, (ii) comprises glycosylated erythropoietin (EPO) in a formulation having a concentration of 100-500 IU/g EPO, (iii) provides uniform and slow release of the EPO in an amount of 50-1,500 IU EPO/cm$^2$ wound area into the wound, and (iv) stabilizes the EPO in said formulation.

2. The gelatinous formulation according to claim 1, wherein the swellable polysaccharide is carboxymethylcellulose in a concentration of 2-3% by weight and wherein the formulation comprises 150 IU EPO/g.

3. The gelatinous formulation according to claim 1, wherein the gel is in or on a solid carrier matrix.

4. The gelatinous formulation according to claim 3, wherein the solid carrier matrix is a three-dimensional structured plaster.

5. The gelatinous formulation according to claim 1, wherein said formulation is obtained by mixing EPO in lyophilized, dissolved or suspended form with the swellabe polysaccharide having a pre-swollen viscosity of less than 5,000 mPa×s.

6. The gelatinous formulation according to claim 1, wherein the formulation affects wound healing by re-epithelialization after 4 to 8 days of between 92% and 99%, compared to between 85% and 87% by applying the same formulation under the same conditions without EPO.

7. The gelatinous formulation of claim 1, wherein the formulation further comprises a disinfectant and/or a proteinase inhibitor.

8. A method of treating a wound in traumatized skin, the method comprising applying the formulation of claim 1.

9. The method of claim 8, wherein the formulation is applied in a single treatment.

10. The method of claim 8, wherein the application of the formulation affects wound healing by re-epithelialization after 4-8 days of between 92 to 99% and said wound healing is 10 to 50% faster than for the same formulation without EPO.

11. The method of claim 8, whereby 1 g of the formulation is applied per cm$^2$ wound area.

12. A process for the manufacture of the formulation of claim 1 comprising:

preparing a pre-swollen polysaccharide preparation having a viscosity of less than 5,000 mPa×s, wherein the polysaccharides and weight percent of polysaccharides are according to claim 1, and mixing EPO in lyophilized, dissolved or suspended form with said pre-swollen polysaccharide preparation by allowing EPO to diffuse in over at least 24 hours until said viscosity is obtained, wherein EPO is used in a concentration of 100 to 500 IU/g of the gelatinous formulation.

* * * * *